United States Patent
Arunakumari et al.

(10) Patent No.: US 11,292,814 B2
(45) Date of Patent: Apr. 5, 2022

(54) CATION EXCHANGE CHROMATOGRAPHY METHODS

(71) Applicant: E.R. SQUIBB & SONS, L.L.C., Princeton, NJ (US)

(72) Inventors: Alahari Arunakumari, Pennington, NJ (US); Jue Wang, Bedminster, NJ (US)

(73) Assignee: E.R. SQUIBB & SONS, L.L.C., Princeton, NJ (US)

( * ) Notice: Subject to any disclaimer, the term of this patent is extended or adjusted under 35 U.S.C. 154(b) by 403 days.

(21) Appl. No.: 15/958,001

(22) Filed: Apr. 20, 2018

(65) Prior Publication Data

US 2019/0119317 A1     Apr. 25, 2019

Related U.S. Application Data

(63) Continuation of application No. 13/497,846, filed as application No. PCT/US2010/049797 on Sep. 22, 2010, now abandoned.

(60) Provisional application No. 61/244,971, filed on Sep. 23, 2009.

(51) Int. Cl.
*C07K 1/16* (2006.01)
*C07K 1/18* (2006.01)

(52) U.S. Cl.
CPC ........................... *C07K 1/18* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. |
| 5,223,409 A | 6/1993 | Ladner et al. |
| 5,225,539 A | 7/1993 | Winter |
| 5,403,484 A | 4/1995 | Ladner et al. |
| 5,427,908 A | 6/1995 | Dower et al. |
| 5,476,996 A | 12/1995 | Wilson et al. |
| 5,530,101 A | 6/1996 | Queen et al. |
| 5,534,615 A | 7/1996 | Baker et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,693,762 A | 12/1997 | Queen et al. |
| 5,698,767 A | 12/1997 | Wilson et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,939,598 A | 8/1999 | Kucherlapati et al. |
| 5,969,108 A | 10/1999 | McCafferty et al. |
| 6,075,181 A | 6/2000 | Kucherlapati et al. |
| 6,114,598 A | 9/2000 | Kucherlapati et al. |
| 6,150,584 A | 11/2000 | Kucherlapati et al. |
| 6,162,963 A | 12/2000 | Kucherlapati et al. |
| 6,172,197 B1 | 1/2001 | McCafferty et al. |
| 6,180,370 B1 | 1/2001 | Queen et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 2001/0051708 A1 * | 12/2001 | Laursen ............ A61K 39/39591 530/387.1 |
| 2003/0054435 A1 * | 3/2003 | Grabski ................ C12N 1/06 435/68.1 |
| 2003/0166062 A1 * | 9/2003 | Gonzalez-Villasenor .................. C07K 1/113 435/69.1 |
| 2009/0148435 A1 * | 6/2009 | Lebreton .................. C07K 1/36 424/130.1 |

FOREIGN PATENT DOCUMENTS

| | | |
|---|---|---|
| WO | WO 92/03918 | 3/1992 |
| WO | WO 93/12227 | 6/1993 |

(Continued)

OTHER PUBLICATIONS

Notice of opposition to a European patent, Patent No. EP2480561, Apr. 13, 2017.
Opposition Brief (Roche) Apr. 13, 2017.
Lain, B., et al., "Development of a High-Capacity MAb Capture Step Based on Cation-Exchange Chromatography," BioProcess Technical, pp. 26-34 (May 2009).
Kohno, A., et al., "Features of the β-amylase isoform system in dry and germinating seeds of alfalfa (*Medicago sativa* L.)," Biochimica et Biophysica Acta 1035 pp., 325-330 (1990).
Extract from Amersham Handbook "Exchange Chromatography & Chromatofocusing, Principles and Methods," (2004).
Fahrner, R.L., et al., "Industrial Purification of Pharmaceutical Antibodies: Development, Operation, and Validation of Chromatography Processes," Biotechnology and Genetic Engineering Reviews, vol. 18, pp. 301-327 (Jul. 2001).

(Continued)

*Primary Examiner* — Gary Counts

(57) ABSTRACT

The present invention provides improved methods of protein purification using CEX chromatography. Such methods generally comprise the steps of: contacting a protein of interest (e.g., an antibody) with a cation exchange resin at a first pH, that is less than the pI of the most acidic isoform of the protein of interest, such that the protein of interest binds to the resin; washing the cation exchange resin at a second pH that is greater than the first pH, but less than the pI of the most acidic isoform of the protein of interest; and eluting the protein of interest from the resin at a third pH that is about equal to or less than the first pH. The methods of the invention are particularly useful for the commercial purification of recombinant therapeutic proteins (e.g., antibodies).

13 Claims, 4 Drawing Sheets

(56) References Cited

FOREIGN PATENT DOCUMENTS

| WO | WO 94/25585 | 11/1994 |
| WO | WO 97/13852 | 4/1997 |
| WO | WO 98/24884 | 6/1998 |
| WO | WO 99/45962 | 9/1999 |
| WO | WO 01/14424 | 3/2001 |
| WO | WO 02/43478 | 6/2002 |
| WO | WO 2007/108955 | 9/2007 |
| WO | WO 08/025747 | 3/2008 |
| WO | WO 2008/025747 | 3/2008 |
| WO | WO 08/087184 | 7/2008 |
| WO | WO 2008/087184 | 7/2008 |
| WO | WO 08/100578 | 8/2008 |
| WO | WO 2009/058812 | 5/2009 |

OTHER PUBLICATIONS

Ishihara, T., et al., "Optimization of elution salt concentration in stepwise elutin of protein chromatography using linear gradient elution data Reducing residual protein A by cation-exchange chromatography in monoclonal antibody purification," Journal of Chromatography A, vol. 1114, pp. 97-101 (2006).

Zhao, Y-Y, et al., "Charge Variants of an Avastin Biosimilar Isolation, Characterization, In Vitro Properties and Pharmacokinetics in Rat," PLOS ONE, pp. 1-13, (Mar. 17, 2016).

Notice of opposition to a European patent, Patent No. EP2480561, Apr. 12, 2017.

Opposition Brief (Glaxo), Apr. 12, 2017.

Vickova, M., et al., "Pharmaceutical applications of isoelectric focusing on microchip with imaged UV detection," Journal of Chromatography A., vol. 1181, pp. 145-152 (2008).

Hayduk, E.J., et al., "A two-dimensional electrophoresis map of Chinese hamster ovary cell proteins based on fluorescence staining," Electrophoresis, vol. 25, pp. 2545-2556 (2004).

Schmidt, C.A., et al., "Physico-Chemical Characterization and Biological Evaluation of Recombinant Human Erythropoietin in Pharmaceutical Products," Lat. A. J. Pharm, vol. 22(4), pp. 343-350 (2003).

Ahamed, T. et al., "Selection of pH-related parameters in ion-exchange chromatography using pH-gradient operations", Journal of Chromatography A, vol. 1194, pp. 22-29 (2008).

Arunakumari, A. et al., "Improved Downstream Process Design for Human Monoclonal Antibody Production", Supplement to Biopharm International, pp. 36-40 (2007).

Chen, J. et al., "B cell development in mice that lack one or both immunoglobulin κ light chain genes", The EMBO Journal, vol. 12, No. 3, pp. 821-830 (1993).

Chen, J. et al., "Immunoglobulin gene rearrangement in B cell deficient mice generated by targeted deletion of the $J_H$ locus", International Immunology, vol. 5, No. 6, pp. 647-656 (1993).

Choi, T.K. et al., "Transgenic mice containing a human heavy chain immunoglobulin gene fragment cloned in a yeast artificial chromosome", Nature Genetics, vol. 4, pp. 117-123, and a correction p. 320 (1993).

Clackson, T. et al., "Making antibody fragments using phage display libraries", Nature, vol. 352, pp. 624-628 (1991).

De Vilmorin, P., "Scale-up Evaluation of Selective Antibody Precipitation and Continuous Recovery with a Disc-Stack Centrifuge", BioProcess International Conference & Exhibition Anaheim, CA, Sep. 23-26, 2008.

Fishwild, D.M. et al., "High-avidity human IgGκ monoclonal antibodies from a novel strain of minilocus transgenic mice", Nature Biotechnology, vol. 14, pp. 845-851 (1996).

Foster, P.R. et al., "The Kinetics of Protein Salting-Out: Precipitation of Yeast Enzymes by Ammonium Sulfate", Biotechnology and Bioengineering, vol. XVIII, pp. 545-580 (1976).

Gagnon, P. et al., "Use of Hydrophobic Interaction Chromatography With a Non-Salt Buffer System for Improving Process Economics in Purification of Monoclonal Antibodies", Tosoh BioScience GMBH, pp. 1-4 (2000).

Jones, P.T. et al., "Replacing the complementarity-determining regions in a human antibody with those from a mouse", Nature, vol. 321, pp. 522-525 (1986).

Köhler, G. et al., "Continuous cultures of fused cells secreting antibody of predefined specificity", Nature, vol. 256, pp. 495-497 (1975).

Kohno, A. et al., "Features of the beta-amylase isoform system in dry and germinating seeds of alfalfa (Medicago sativa L.)", Biochimica et Biophysica ACTA—General Subjects, vol. 1035, No. 3, pp. 325-330 (1990).

Marks, J.D. et al., "By-passing Immunization—Human Antibodies from V-gene Libraries Displayed on Phage", J. Mol. Biol., vol. 222, pp. 581-597 (1991).

Matheus, S. et al., "Liquid High Concentration IgG1 Antibody Formulations by Precipitation", Journal of Pharmaceutical Sciences, vol. 98, No. 9, pp. 3043-3057 (2009).

Morrison, S.L. et al., "Chimeric human antibody molecules: Mouse antigen-binding domains with human constant region domains", Proc. Natl. Acad. Sci. USA, vol. 81, pp. 6851-6855 (1984).

Moscariello, J., "Comparison of Potential Monoclonal Antibody Purification Processes with Two Chromatography Steps", BioProcess International Conference & Exhibition, Anaheim, CA, Sep. 23-26, 2008.

Presta, L.G., "Antibody engineering", Current Opinion in Structural Biology, vol. 2, pp. 593-596 (1992).

Riechmann, L., et al., "Reshaping human antibodies for therapy", Nature, vol. 332, pp. 323-327 (1988).

Shields, C., "Advances in Single Use Capture Chromatography", BioProcess International Conference & Exhibition, Anaheim, CA, Sep. 23-26, 2008.

Taylor, L.D. et al., "A transgenic mouse that expresses a diversity of human sequence heavy and light chain immunoglobulins", Nucleic Acids Research, vol. 20, No. 23, pp. 6287-6295 (1992).

Taylor, L.D. et al., "Human immunoglobulin transgenes undergo rearrangement, somatic mutation and class switching in mice that lack endogenous IgM", International Immunology, vol. 6, No. 4, pp. 579-591 (1994).

Tuaillon, N. et al., "Biased Utilization of $D_{HQ52}$ and $J_H4$ Gene Segments in a Human Ig Transgenic Minilocus Is Independent of Antigenic Selection", Journal of Immunology, vol. 152, pp. 2912-2920 (1994).

Tuaillon, N. et al., "Human immunoglobulin heavy-chain minilocus recombination in transgenic mice: Gene-segment use in μ and γ transcripts", Proc. Natl. Acad. Sci. USA, vol. 90, pp. 3720-3724 (1993).

Wang, J. et al., "Optimizing the Primary Recovery Step in Nonaffinity Purification Schemes for HuMAbs", BioPharm International, pp. 1-9 (2008).

Zellner, M. et al., "Quantitative validation of different protein precipitation methods in proteome analysis of blood platelets", Electrophoresis, vol. 26, pp. 2481-2489 (2005).

International Search Report for—PCT/US2010/049797, dated Dec. 6, 2010 (4 pages).

Jun Dai, et al., "Capillary Isoelectric Focusing-Mass Spectrometry Method for the Separation and Online Characterization of Intact Monoclonal Antibody Charge Variants", Analytical Chemistry, 2018, vol. 90, pp. 2246-2254.

Mariana P. Miranda-Hernandez, et al., "Assessment of Physicochemical Properties of Rituximab Related to Its Immunomodulatory Activity", Journal of immunology Research, vol. 2015, 2014, pp. 1-11.

* cited by examiner

HCP contaminants bound to column at pH 6.2 along with antibodies with pI of 8.6

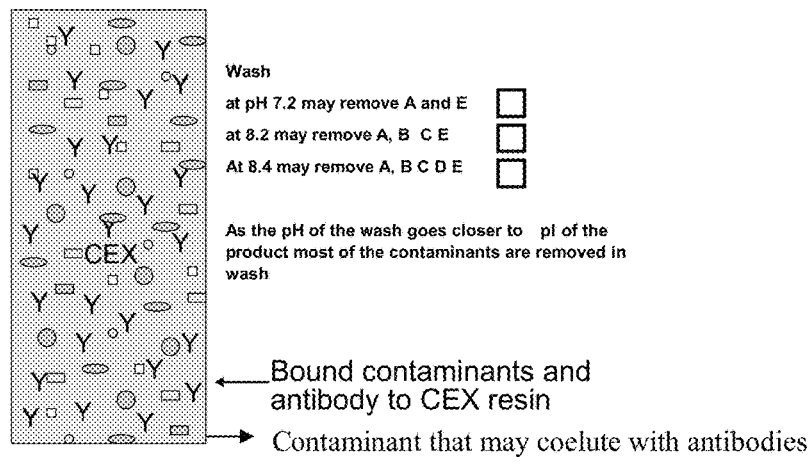

Elution

Lower the elution pH compared to wash pH, lesser the HCP.

Ex: With pH 7.2 wash, Elution at pH 4.5 will have lesser HCP than elution at pH 6.2

Higher the elution pH compared to wash pH, more the HCP

Ex: Elution at pH 7.5 which is higher than wash pH may contain most of the contaminants (( Ab+B+ C+ D)

Wash
at pH 7.2 may remove A and E ☐
at 8.2 may remove A, B C E ☐
At 8.4 may remove A, B C D E ☐

As the pH of the wash goes closer to pI of the product most of the contaminants are removed in wash ← Bound contaminants and antibody to CEX resin → Contaminant that may coelute with antibodies

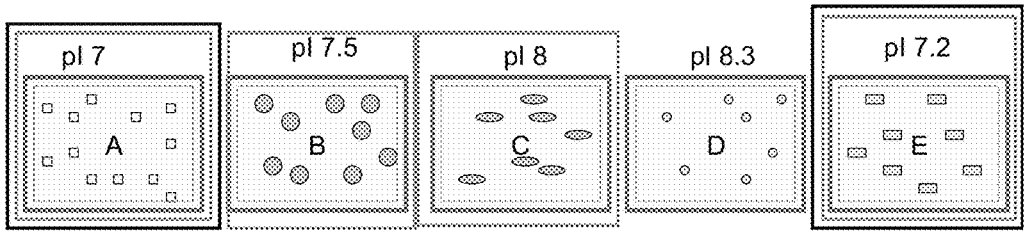

CATION EXCHANGE CHROMATOGRAPHY METHODS

CROSS-REFERENCE TO RELATED APPLICATIONS

This application is a continuation of U.S. application Ser. No. 13/497,846 filed Mar. 23, 2012, now abandoned, which is a 371 filing of PCT/US2010/049797 filed Sep. 22, 2010, which claims priority to U.S. Provisional Application Ser. No. 61/244,971 filed Sep. 23, 2009, the entire contents of all of which are herein incorporated by reference.

BACKGROUND OF THE INVENTION

Large-scale, economic purification of proteins is an increasingly important challenge for the biopharmaceutical industry. Therapeutic proteins are typically produced using prokaryotic or eukaryotic cell lines that are engineered to express the protein of interest from a recombinant plasmid containing the gene encoding the protein. Separation of the desired protein from the mixture of components fed to the cells and cellular by-products to an adequate purity, e.g., sufficient for use as a human therapeutic, is a fundamental requirement for biologics manufacturers. However, in therapeutic antibody purification, the current industry-standard, chromatography capture resin, Protein A, is expensive, has a relatively low throughput, and limited life cycles.

Accordingly there is a need in the art for alternative protein purification methods that can be used to expedite the large-scale processing of protein-based therapeutics, such as antibodies, especially due to escalating high titers from cell culture.

SUMMARY OF THE INVENTION

The present invention provides improved methods for protein purification using cation exchange (CEX) chromatography. These methods generally involve contacting a protein of interest (e.g., an antibody) with a cation exchange resin at a first pH that is less than the isoelectric point (pI) of the most acidic isoform of the protein of interest, such that the protein of interest binds to the resin. The resin is then washed at a second pH that is greater than the first pH, but less than the pI of the most acidic isoform of the protein of interest. The protein is subsequently eluted from the resin at a third pH that is about equal to or less than the first pH. This combination of higher pH wash and lower pH elution results in improved separation of the protein of interest (e.g., an antibody) from contaminants (e.g., HCP), compared to conventional CEX purification methods. The methods of the invention are useful for the commercial purification of recombinant therapeutic proteins, particularly antibodies.

Accordingly, in one aspect, the invention provides a method of purifying a protein of interest from a mixture comprising the protein of interest and one or more contaminants, the method comprising the steps of: (A) determining the pI of the most acidic isoform of the protein of interest; (B) contacting the protein of interest with a cation exchange resin at a first pH that is less than the pI of the most acidic isoform of the protein of interest, such that the protein of interest binds to the resin; (C) washing the cation exchange resin at a second pH that is greater than the first pH, but less than the pI of the most acidic isoform of the protein of interest; and (D) eluting the protein of interest from the resin at a third pH that is about equal to or less than the first pH, thereby purifying the protein of interest.

In a particular embodiment, the first pH is between about pH 4 and about pH 8.2, for example, between about pH 4.5 and about pH 6.2 (e.g., at 4.5, 4.6, 4.7, 4.8, 4.9, 5.0, 5.1, 5.2, 5.3, 5.4, 5.5, 5.6, 5.7, 5.8, 5.9, 6.0, 6.1 or 6.2), where the pI of the most acidic isoform of the protein of interest is between about pI 7 and about pI 9, for example between about pI 7.3 and about pI 8. Exemplary pIs and pHs are shown in Table 1 and Table 2.

In certain embodiments, the second pH is greater than the first pH, but is about 0.1 to about 1.2 pH units less than the pI of the most acidic isoform of the protein of interest. In a particular embodiment, the second pH is between about pH 6 and about pH 8.2 (e.g., at 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1 or 8.2). Exemplary pHs are shown in Table 1 and Table 2.

In certain embodiments, the third pH is about equal to or less than the first pH. In a particular embodiment, the third pH is between about 4 and about 8.2, for example, between about 4.5 and about 6.2 (e.g., at 4.5, 4.6, 4.7, 4.8, 4.9, 5.0, 5.1, 5.2, 5.3, 5.4, 5.5, 5.6, 5.7, 5.8, 5.9, 6.0, 6.1 or 6.2). An exemplary pH (6.2) is shown in Table 1 and Table 2.

The starting mixture may comprise any combination of proteins. In one embodiment, the mixture comprises clarified bulk, such as a cell culture supernatant (e.g., a mammalian, bacterial, plant or fungal cell culture). Typical cell culture supernatants include, without limitation, CHO and NS0 cell cultures.

The methods of the invention can be used to purify any type of protein from a mixture. In a particular embodiment, the protein is an antibody, such as a monoclonal antibody (e.g., a human, humanized or chimeric monoclonal antibody) or a fragment thereof.

BRIEF DESCRIPTION OF THE DRAWING

FIG. 4 shows a schematic of the relationship between loading, wash, and elution pH and the contaminants present in a protein sample purified by CEX chromatography.

DETAILED DESCRIPTION OF THE INVENTION

Definitions

Figure 1:
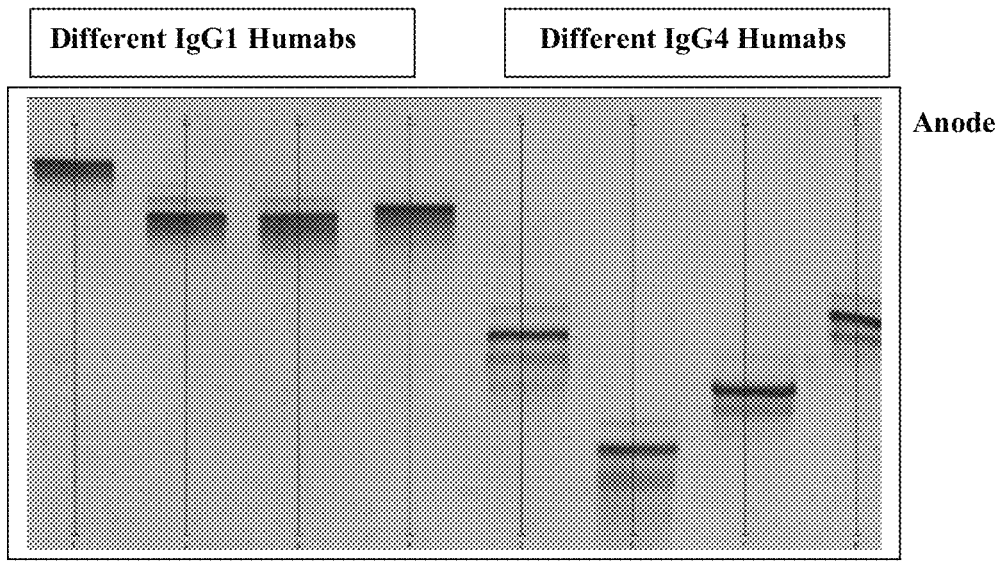
FIG. 1 shows an isoelectric focus (IEF) gel of IgG1 and IgG4 human antibodies (Humabs).
Figure 2:
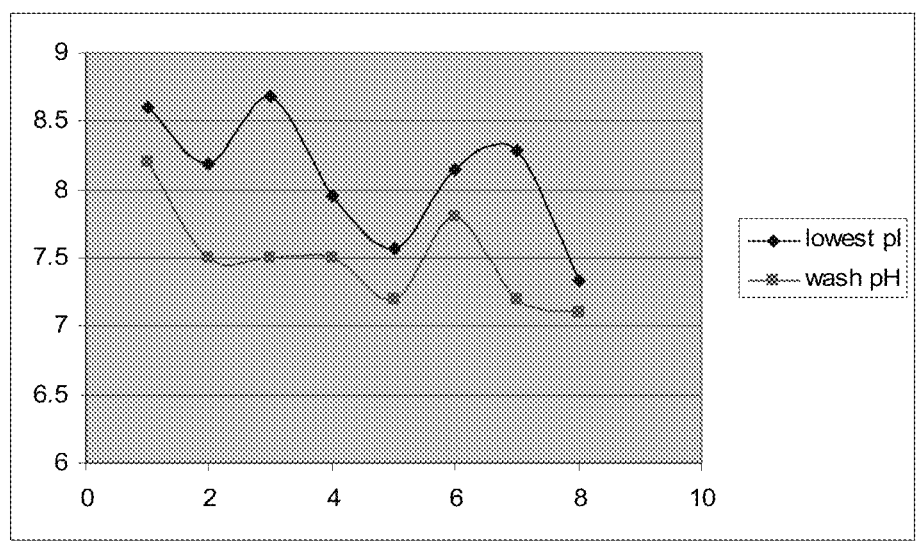
FIG. 2 shows a graph of the relationship between CEX wash pH and the lowest pI of the Humab for the Humabs listed in Table 1.

As used herein, the terms "purifying" and "separating" are used interchangeably, and refer to the removal of contaminants from a mixture containing a protein of interest (e.g., an antibody).

As used herein, the term "protein of interest" is used in its broadest sense to include any protein (either natural or recombinant), present in a mixture, for which purification is desired. Such proteins of interest include, without limitation, hormones, growth factors, cytokines, immunoglobulins (e.g., antibodies), immunoglobulin-like domain-containing molecules (e.g., ankyrin or fibronectin domain-containing molecules), and Fc-fusion proteins. The term "Fc-fusion protein", as used herein, is meant to encompass therapeutic proteins comprising an immunoglobulin-derived moiety (i.e., an Fc moiety) and a moiety derived from a second, non-immunoglobulin protein.

As used herein, a "mixture" comprises a protein of interest (for which purification is desired) and one or more contaminant, i.e., impurities. In one embodiment, the mixture is produced from a host cell or organism that expresses the protein of interest (either naturally or recombinantly). Such mixtures include, for example, cell cultures, cell lysates, and clarified bulk (e.g., clarified cell culture supernatant).

As used herein, the term "contaminant" is used in its broadest sense to cover any undesired component or compound within a mixture. In cell cultures, cell lysates or clarified bulk (e.g., cell culture supernatant), contaminants include, for example, host cell nucleic acids (e.g., DNA) and host cell proteins present in a cell culture medium. Host cell contaminant proteins include, without limitation, those naturally or recombinantly-produced by the host cell, as well as proteins related to or derived from the protein of interest (e.g., proteolytic fragments) and other process related contaminants (e.g., truncated and aggregated versions of the protein of interest).

As used herein, "isoform" refers to any form or variant of a protein of interest distinguishable by its pI. Typical isoforms include, without limitation, glycoforms (i.e., proteins with differing carbohydrate moieties) and aminated variants. The "most acidic" isoform of a protein is the isoform having the lowest pI value. Any art recognized method can be used to determine or predict the isoelectric point (pI) of the different isoforms of a protein of interest. Suitable techniques include, without limitation, IEF and calculation using the known pKa of each charged group of the protein of interest. Previously determined or commonly accepted pI values for the isoforms of a protein of interest can also be used to employ the methods of the invention.

As used herein, "washing" refers to passing an appropriate buffer through or over a cation exchange resin.

As used herein, "eluting" refers to removing a protein of interest (e.g., an antibody) from a cation exchange resin, by altering the ionic strength of the buffer surrounding the cation exchange resin such that the buffer competes with the molecule for the charged sites on the ion exchange material.

As used herein, a "cell culture" refers to cells in a liquid medium that produce a protein of interest. The cells can be from any organism including, for example, bacteria, fungus, mammals or plants. Suitable liquid media include, for example, nutrient media and non-nutrient media.

As used herein, the term "clarified bulk" refers to a mixture from which particulate matter (e.g., cells) has been substantially removed. Clarified bulk includes cell culture supernatant, or cell lysate from which cells or cell debris has been substantially removed by, for example, filtration or centrifugation.

The term "antibody" is used in the broadest sense to cover any type of known antibody, including, but is not limited to, monoclonal antibodies (including full length monoclonal antibodies), polyclonal antibodies, monospecific antibodies, multispecific antibodies (e.g., bispecific antibodies), immunoadhesins, antibody-immunoadhesin chimeras, humanized, human, chimeric, single-chain, synthetic, recombinant, hybrid, mutated, grafted, or in vitro generated antibodies. The antibody can be a full length antibody or an antibody fragment. The antibody may be selected from any of the known antibody isotypes, for example, IgA, IgG, IgD, IgE, IgM. The antibody may be a monomer, dimer, or multimer (e.g., a trimer or pentamer).

An "antibody fragment" includes at least a portion of a full length antibody and typically an antigen binding or variable region thereof. Examples of antibody fragments include Fab, Fab', F(ab')$_2$, and Fv fragments; single-chain antibody molecules; diabodies; linear antibodies; and multispecific antibodies formed from engineered antibody fragments.

The term "monoclonal antibody" is used in the conventional sense to refer to an antibody obtained from a population of substantially homogeneous antibodies such that the individual antibodies comprising the population are identical except for possible naturally occurring mutations that may be present in minor amounts. Monoclonal antibodies are highly specific, being directed against a single antigenic site. This is in contrast with polyclonal antibody preparations which typically include varied antibodies directed against different determinants (epitopes) of an antigen, whereas monoclonal antibodies are directed against a single determinant on the antigen. The term "monoclonal", in describing antibodies, indicates the character of the antibody as being obtained from a substantially homogeneous population of antibodies, and is not to be construed as requiring production of the antibody by any particular method. For example, monoclonal antibodies used in the present invention can be produced using conventional hybridoma technology first described by Kohler et al., Nature 256:495 (1975), or they can be made using recombinant DNA methods (see, e.g., U.S. Pat. No. 4,816,567). Monoclonal antibodies can also be isolated from phage antibody libraries, e.g., using the techniques described in Clackson et al., Nature 352:624-628 (1991); Marks et al., J. Mol. Biol. 222:581-597 (1991); and U.S. Pat. Nos. 5,223,409; 5,403,484; 5,571,698; 5,427,908 5,580,717; 5,969,108; 6,172,197; 5,885,793; 6,521,404; 6,544,731; 6,555,313; 6,582,915; and 6,593,081.

Monoclonal antibodies described herein include "chimeric" and "humanized" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)). "Humanized" forms of non-human (e.g., murine) antibodies are chimeric antibodies which contain minimal sequence derived from non-human immunoglobulin. For the most part, humanized antibodies are human immunoglobulins (recipient antibody) in which the hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

Chimeric or humanized antibodies can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

The monoclonal antibodies described herein also include "human" antibodies, which can be isolated from various sources, including, e.g., from the blood of a human patient or recombinantly prepared using transgenic animals. Examples of such transgenic animals include KM-Mouse® (Medarex, Inc., Princeton, N.J.) which has a human heavy chain transgene and a human light chain transchromosome (see WO 02/43478), Xenomouse® (Abgenix, Inc., Fremont Calif.; described in, e.g., U.S. Pat. Nos. 5,939,598; 6,075,181; 6,114,598; 6,150,584 and 6,162,963 to Kucherlapati et al.), and HuMAb-Mouse® (Medarex, Inc.; described in, e.g., Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, U.S. Pat. Nos. 5,545,806; 5,569,825; 5,625,126; 5,633,425; 5,789,650; 5,877,397; 5,661,016; 5,814,318; 5,874,299; and 5,770,429; 5,545,807; and PCT Publication Nos. WO 92/03918, WO 93/12227, WO 94/25585, WO 97/13852, WO 98/24884 and WO 99/45962, WO 01/14424 to Korman et al.). Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

As used herein the term "chromatography" refers to the process by which a solute of interest, e.g., a protein of interest, in a mixture is separated from other solutes in the mixture by percolation of the mixture through an adsorbent, which adsorbs or retains a solute more or less strongly due to properties of the solute, such as pI, hydrophobicity, size and structure, under particular buffering conditions of the process.

The terms "ion-exchange" and "ion-exchange chromatography" refer to a chromatographic process in which an ionizable solute of interest (e.g., a protein of interest in a mixture) interacts with an oppositely charged ligand linked (e.g., by covalent attachment) to a solid phase ion exchange material under appropriate conditions of pH and conductivity, such that the solute of interest interacts non-specifically with the charged compound more or less than the solute impurities or contaminants in the mixture. The contaminating solutes in the mixture can be washed from a column of the ion exchange material or are bound to or excluded from the resin, faster or slower than the solute of interest. "Ion-exchange chromatography" specifically includes cation exchange (CEX), anion exchange, and mixed mode chromatographies.

A "cation exchange resin" or "CEX resin" refers to a solid phase which is negatively charged, and which has free cations for exchange with cations in an aqueous solution passed over or through the solid phase. Any negatively charged ligand attached to the solid phase suitable to form the cation exchange resin can be used, e.g., a carboxylate, sulfonate and others as described below. Commercially available cation exchange resins include, but are not limited to, for example, those having a sulfonate based group (e.g., MonoS, MiniS, Source 15S and 30S, SP Sepharose Fast Flow™, SP Sepharose High Performance from GE Healthcare, Toyopearl SP-650S and SP-650M from Tosoh, Macro-Prep High S from BioRad, Ceramic HyperD S, Trisacryl M and LS SP and Spherodex LS SP from Pall Technologies); a sulfoethyl based group (e.g., Fractogel SE, from EMD, Poros S-10 and S-20 from Applied Biosystems); a sulphopropyl based group (e.g., TSK Gel SP 5PW and SP-5PW-HR from Tosoh, Poros HS-20 and HS 50 from Applied Biosystems); a sulfoisobutyl based group (e.g., (Fractogel EMD $SO_3^-$ from EMD); a sulfoxyethyl based group (e.g., SE52, SE53 and Express-Ion S from Whatman), a carboxymethyl based group (e.g., CM Sepharose Fast Flow from GE Healthcare, Hydrocell CM from Biochrom Labs Inc., Macro-Prep CM from BioRad, Ceramic HyperD CM, Trisacryl M CM, Trisacryl LS CM, from Pall Technologies, Matrx Cellufine C500 and C200 from Millipore, CM52, CM32, CM23 and Express—Ion C from Whatman, Toyopearl CM-650S, CM-650M and CM-650C from Tosoh); sulfonic and carboxylic acid based groups (e.g., BAKER-BOND Carboxy-Sulfon from J. T. Baker); a carboxylic acid based group (e.g., WP CBX from J. T Baker, DOWEX MAC-3 from Dow Liquid Separations, Amberlite Weak Cation Exchangers, DOWEX Weak Cation Exchanger, and Diaion Weak Cation Exchangers from Sigma-Aldrich and Fractogel EMD COO—from EMD); a sulfonic acid based group (e. g., Hydrocell SP from Biochrom Labs Inc., DOWEX Fine Mesh Strong Acid Cation Resin from Dow Liquid Separations, UNOsphere S, WP Sulfonic from J. T. Baker, Sartobind S membrane from Sartorius, Amberlite Strong Cation Exchangers, DOWEX Strong Cation and Diaion Strong Cation Exchanger from Sigma-Aldrich); and a orthophosphate based group (e.g., P11 from Whatman).

Mixtures Containing a Protein of Interest

The methods of the invention can be applied to purify one or more protein(s) of interest from any mixture containing the protein(s). In one embodiment, the mixture is obtained from or produced by living cells that express the protein to be purified (e.g., naturally or by genetic engineering). Methods of genetically engineering cells to produce proteins are well known in the art. See e.g., Ausabel et al., eds. (1990), Current Protocols in Molecular Biology (Wiley, New York) and U.S. Pat. Nos. 5,534,615 and 4,816,567, each of which is specifically incorporated herein by reference. Such methods include introducing nucleic acids that encode and allow expression of the protein into living host cells. These host cells can be bacterial cells, fungal cells, or, preferably, animal cells grown in culture. Bacterial host cells include, but are not limited to *E. coli* cells. Examples of suitable *E. coli* strains include: HB101, DH5α, GM2929, JM109, KW251, NM538, NM539, and any *E. coli* strain that fails to cleave foreign DNA. Fungal host cells that can be used include, but are not limited to, *Saccharomyces cerevisiae*, *Pichia pastoris* and *Aspergillus* cells. A few examples of animal cell lines that can be used are CHO, VERO, DXB11, BHK, HeLa, Cos, MDCK, 293, 3T3, NS0 and WI138. New animal cell lines can be established using methods well know by those skilled in the art (e.g., by transformation, viral infection, and/or selection). In other embodiments, the protein of interest (e.g., an antibody) is produced in a CHO cell (see, e.g., WO 94/11026). Various types of CHO cells are known in the art, e.g., CHO-K1, CHO-DG44, CHO-DXB11, CHO/dhfr⁻ and CHO-S.

Preparation of mixtures initially depends on the manner of expression of the protein. Some cell systems directly secrete the protein (e.g., an antibody) from the cell into the surrounding growth media, while other systems retain the antibody intracellularly. For proteins produced intracellularly, the cell can be disrupted using any of a variety of methods, such as mechanical shear, osmotic shock, and enzymatic treatment. The disruption releases the entire contents of the cell into the homogenate, and in addition produces subcellular fragments which can be removed by centrifugation or by filtration. A similar problem arises, although to a lesser extent, with directly secreted proteins due to the natural death of cells and release of intracellular host cell proteins during the course of the protein production run.

In one embodiment, cells or cellular debris are removed from the mixture, for example, to prepare clarified bulk. The methods of the invention can employ any suitable methodology to remove cells or cellular debris, including, centrifugation, tangential flow filtration or depth filtration.

Protein Purification

The methods of the invention provide improved techniques for CEX purification of a protein of interest (e.g., an antibody) from a mixture. These methods generally comprise the steps of: (A) contacting the protein of interest with a cation exchange resin at a first pH that is less than the pI of the most acidic isoform of the protein of interest, such that the protein of interest binds to the resin; (B) washing the cation exchange resin at a second pH that is greater than the first pH, but less than the pI of the most acidic isoform of the protein of interest; and (C) eluting the protein of interest from the resin at a third pH that is about equal to or less than the first pH. However, the skilled artisan will appreciate that additional purification can be performed before, after or in between the steps of the aforementioned method. The combination of higher pH wash and lower pH elution employed in the methods of the invention results in efficient separation of the protein of interest (e.g., an antibody) from contaminants (e.g., HCP), compared to that achieved using conventional CEX purification methods.

TABLE 1 pI Ranges and CEX Load, Wash and Elution pHs For Eight Humabs

| Product | pI range | lowest pI | CEX wash pH | ΔpH (lowest pI − wash pH) | CEX load pH | CEX elution pH |
|---|---|---|---|---|---|---|
| Humab-1 | 8.60-8.81 | 8.6 | 8.2 | 0.4 | 6.2 | 6.2 |
| Humab-2 | 8.19-8.50 | 8.19 | 7.5 | 0.69 | 6.2 | 6.2 |
| Humab-3 | 8.68-8.83 | 8.68 | 7.5 | 1.18 | 6.2 | 6.2 |
| Humab-4 | 7.96-8.39 | 7.96 | 7.5 | 0.46 | 6.2 | 6.2 |
| Humab-5 | 7.57-8.18 | 7.57 | 7.2 | 0.37 | 6.2 | 6.2 |
| Humab-6 | 8.14-8.49 | 8.14 | 7.8 | 0.34 | 5.7 | 6.2 |
| Humab-7 | 8.28-8.78 | 8.28 | 7.2 | 1.08 | 6.2 | 6.2 |
| Humab-8* | 7.33-8.21 | 7.33 | 7.1 | 0.23 | 6.2 | 6.2 |

*Humab-8 is a IgG4 molecule

Table 1 shows exemplary binding, wash and elution pHs for the CEX purification of eight human monoclonal antibodies according to the methods of the invention. FIG. 4 schematically shows particular embodiments of the methods.

Any methods can be used to determine the pI of the most acidic isoform of the protein of interest (e.g., an antibody). Such methods include, without limitation, isoelectric focusing (IEF) techniques, and manual or in silico calculation using the known pKas of the charged groups of the protein of interest. An example of IEF determination of the pI of the different isoforms of eight human antibodies is shown in FIG. 1. However, the skilled artisan will appreciate that, if the pI values for the various isoforms of a protein are already known, it is not necessary for them to be determined again in order to practice the methods of the invention.

Binding of the protein of interest (e.g., an antibody) to a cation exchange resin can be performed at any pH below the pI of the most acidic isoform of the protein to be purified. In particular embodiments, the protein of interest (e.g., an antibody) is bound to the resin between about pH 4 and about pH 8 (e.g., about pH 4, 4.5, 5, 5.5, 6, 6.5, 7, 7.5, and 8). In one exemplified embodiment, the protein of interest (e.g., an antibody) is bound to the resin at about pH 6.2. In another exemplified embodiment, the protein of interest (e.g., an antibody) is bound to the resin at about pH 4.5.

Once the protein (e.g., an antibody) is bound to the cation exchange resin, contaminants (e.g., HCP) are removed by washing the resin with a buffer at a second pH that is greater than the first pH, but less than the pI of the most acidic isoform of the protein. The optimal pH for washing the resin can be determined empirically for each protein of interest by monitoring the purity and yield of the purified protein. In certain embodiments, the resin is washed at a pH of between about 0.1 and about 2.0 pH units below the pI of the protein of interest, more preferably between about 0.1 and about 1.2 pH units below the pI (e.g., about 0.2, 0.3, 0.4, 0.5, 0.6, 0.7, 0.8, 0.9, 1.0 and 1.1 pH units below the pI). Table 1 shows exemplary wash pHs relative to pI for the CEX purification of nine human monoclonal antibodies according to the methods of the invention. The wash buffer can be augmented with detergents or surfactants (e.g., polysorbate) to further remove contaminants, e.g., DNA and endotoxin contaminants.

After washing the cation exchange resin, the protein of interest is eluted using a buffer with a pH about equal to, or less than, the binding pH. In certain embodiments, the elution pH (third pH) is between about 0 and about 3 pH units below the binding pH (first pH). In one particular embodiment, the elution pH is about pH 6.2. In another particular embodiment, the elution pH is about pH 4.5. In general, the elution is facilitated by increasing the ionic strength of the elution buffer relative to the binding buffer, for example, by the addition of a salt (e.g., sodium chloride) to the elution buffer. In addition, a polyether (e.g., polyethylene glycol) can be added to the elution buffer to reduce protein aggregation and the formation of higher molecular weight species.

The present disclosure is further illustrated by the following examples, which should not be construed as further limiting. The contents of all figures and all references, patents and published patent applications cited throughout this application are expressly incorporated herein by reference in their entireties.

Example 1

In this Example a Humab (Humab-1 in table 1) was purified by CEX chromatography using different combinations of load, wash and elution pHs. In all experiments the CEX resin (Poros 50HS (Applied Biosystem)) was packed in a 1 mL column (Φ 0.5 cm×H 5 cm).

Figure 3:
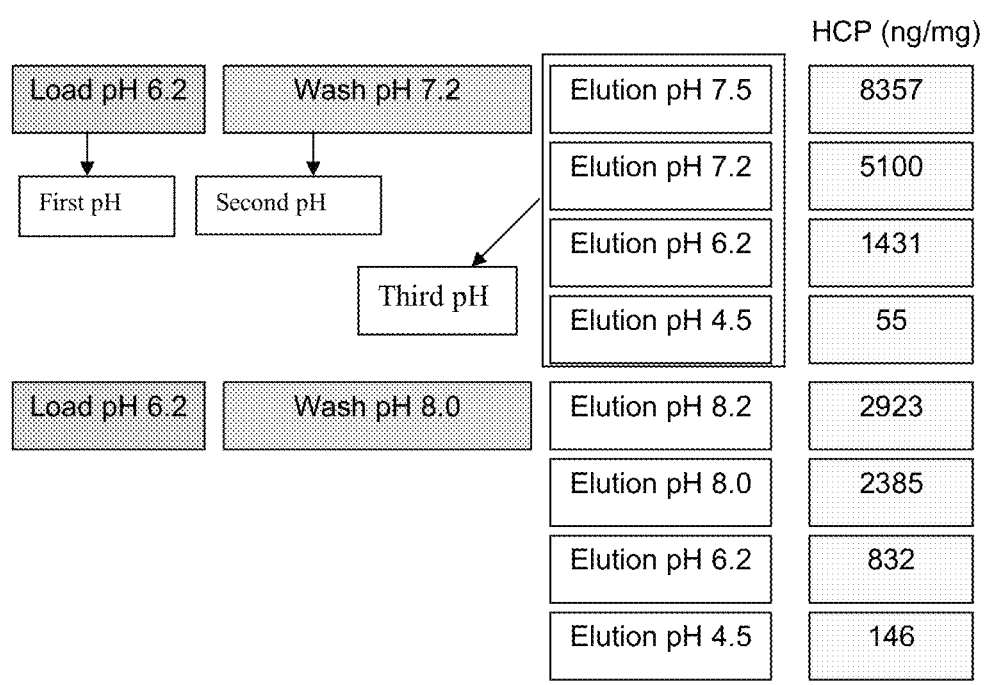
FIG. 3 shows the effects of loading, wash and elution pH on the Host Cell Protein (HCP) content of the eluted Humab when the loading pH is (A) 6.2 and (B) 4.5.
Figure 3:
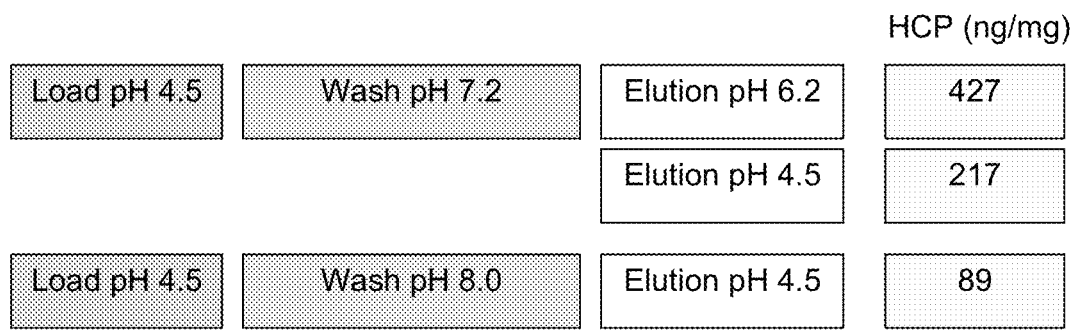

In one set of experiments (FIG. 3A), a CEX column was equilibrated with Sodium Phosphate buffer at pH 6.2 and 5.8 mS/cm. A solution of Humab-1 was adjusted to pH 6.2 and 5.8 mS/cm, and loaded onto the column at a concentration of 15 mg/mL. The column was then washed with Sodium Phosphate and Sodium Chloride dual buffer at pH 7.2 or Sodium Phosphate buffer at pH 8.0. After the wash step, the Humab was eluted from the column at pH 8.2, 8.0, 7.5, 7.2, 6.2, or 4.5 with Sodium Phosphate buffer containing sufficient Sodium Chloride to reach the appropriate conductivity for elution.

In another set of experiments (FIG. 3B), a CEX column was equilibrated with Sodium Citrate and Sodium Phosphate dual buffer at pH 4.5 and 2 mS/cm. A solution of Humab-1 was adjusted to pH 4.5 and 2 mS/cm, and loaded onto the column at a concentration of 15 mg/ml. The column was then washed with Sodium Phosphate and Sodium Chloride dual buffer at pH 7.2 or Sodium Phosphate buffer at pH 8.0. After the wash step, the Humab was eluted from the column at pH 6.2, or 4.5 with Sodium Phosphate buffer containing sufficient Sodium Chloride to reach the appropriate conductivity for elution.

These data demonstrate that if the elution pH is lower than wash pH, preferably about equal to or below the load pH, the greatest removal of host cell contaminants will result. It also illustrates that the best purity of the Humab can be achieved when the wash buffer pH is kept below the pI of the most acidic isoform of the molecule, but as high as possible without washing the Humab off the column.

Example 2

In this Example IgG1 (Humab-4 in table 1) and IgG4 (Humab-8 in table 1) Humabs were purified using the methods of the invention (see Table 2). A CEX column was equilibrated to pH 6.2. Unpurified bulk containing either Humab-4 or Humab-8 was buffer-exchanged to the same pH and ionic strength as the column equilibration buffer and loaded onto a cation exchange column. The column was then washed with Sodium Phosphate buffer at a pH just below the pI of each Humab. After the wash step, the Humabs were eluted from the column with a buffer comprising either 35 mM Sodium Phosphate, 75 mM NaCl at pH 6.2 (Humab-1) or 75 mM Sodium Phosphate, pH 6.2 (for Humab-8).

The data in Table 2 show that the CEX chromatography methods of the invention resulted in about a 1000-fold reduction in the HCP contaminant for both Humab-1 and Humab-8.

TABLE 2

IgG1 and IgG4 Humab Purification Using the Methods of the Invention

| | Humab-4 (IgG1) (lowest pI 7.96) | | | | Humab-8 (IgG4) (lowest pI 7.33) | | |
|---|---|---|---|---|---|---|---|
| Step | Solution | CHO HCP (ng/mg) | DNA (pg/mg) | Step | Solution | CHO HCP (ng/mg) | DNA (pg/mg) |
| Equilibration | 70 mM Sodium Phosphate, pH 6.2 | | | Equilibration | 35 mM Sodium Phosphate, pH 6.2 | | |
| Load | Unprocessed bulk (pH 6.2) | $2.6 \times 10^4$ | $2.6 \times 10^4$ | Load | Unprocessed bulk (pH 6.2) | 108,615 | 808 |
| Post Load Wash | 10 mM Sodium Phosphate, 0.1% Polysorbate 80, pH 7.5 | | | Post Load Wash | 10 mM Sodium Phosphate, 0.5% Polysorbate-80, pH 7.1 | | |
| Elution | 35 mM Sodium Phosphate, 75 mM NaCl, pH 6.2 | 21.9 | 39.5 | Elution | 75 mM Sodium Phosphate, pH 6.2 | 1,294 | 25 |

EQUIVALENTS

Those skilled in the art will recognize or be able to ascertain using no more than routine experimentation, many equivalents of the specific embodiments of the invention described herein. Such equivalents are intended to be encompassed by the following claims.

INCORPORATION BY REFERENCE

All patents, pending patent applications, and other publications cited herein are hereby incorporated by reference in their entireties.

REFERENCES

Ahamed, T., et al. (2007) Selection of pH-related parameters in ion-exchange chromatography using pH-gradient operations. Journal of Chromatography A., 1194(1):22-29. Available online Dec. 8, 2007.

Arunakumari, A., Wang J. and G. Ferreira. (2007). Alternatives to Protein A: Improved Downstream Process Design for Human Monoclonal Antibody Production. Biopharm International, Feb. 2, 2007.

Foster P. R., Dunnill, P. and M. D. Lilly. (2004). "The kinetics of protein salting-out: precipitation of yeast enzymes by ammonium sulfate". Biotechnology and Bioengineering, 18(4): 545-580.

Gagnon, P. (1996) "Purification Tools for Monoclonal Antibodies". Validated Biosystems, Tucson, Ariz. (ISBN: 0-9653515-9-9).

Gagnon, P. (2000). "Use of Hydrophobic Interaction Chromatography with a Non-Salt Buffer System for Improving Process Economics in Purification of Monoclonal Antibodies". Waterside Conference on Monoclonal and Recombinant Antibodies, Miami Fla., Tosoh.

Matheus, S., Friess, W., Schwartz, D. And Mahler H C. (2008). "Liquid high concentration IgG1 antibody formulations bt precipitation". Journal of Pharmaceutical Sciences (Epub ahead of print).

Moscariello, J. (2008). "Comparison of Potential Monoclonal Antibody Purification Processes with Two Chromatography Steps". BioProcess International Conference, Anaheim, Calif.

Shields, Chris. (2008). "Advances in Single Use Capture Chromatography". BioProcess International Conference, Anaheim, Calif.

Ramanan, S. and Stenson, R. (2008). Method of Isolating Antibodies by Precipitation. WO 2008/100578 A2.

Vilmorin, P. (2008). "Scale-up evaluation of selective antibody precipitation and continuous recovery with a disc-stack centrifuge". BioProcess International Conference, Anaheim, Calif.

Wang, J. Diehl, T., Watkins-Fischl, M., Perkins, D., Aguiar, D., and A. Arunakumari. (2008). "Optimizing the primary recovery step in nonaffinity purification schemes for HuMAbs". BioPharm International, Mar. 2, 2008.

Zellner, et al. "Quantitative validation of different protein precipitation methods in proteome analysis of blood platelets". Electrophoresis, 2005 June; 26(12):2481-9.

We claim:

1. A method of purifying a protein of interest from a mixture comprising the protein of interest and one or more contaminants, consisting of:
   (a) determining the pI of the most acidic isoform of the protein of interest;
   (b) contacting the protein of interest with a cation exchange resin at a first pH that is less than the pI of the most acidic isoform of the protein of interest, such that the protein of interest binds to the resin;
   (c) washing the cation exchange resin at a second pH that is greater than the first pH, but about 0.1 to about 0.6 pH units less than the pI of the most acidic isoform of the protein of interest; and
   (d) eluting the protein of interest from the resin at a third pH that is about equal to or less than the first pH, thereby purifying the protein of interest.

2. The method of claim 1, wherein the first pH is about 6.2.

3. The method of claim 1, wherein the third pH is about 4.5.

4. The method of claim 1, wherein the mixture comprises clarified bulk.

5. The method of claim 1, wherein the clarified bulk comprises a cell culture supernatant.

6. The method of claim 5, wherein the supernatant is from a mammalian, bacterial or fungal cell culture.

7. The method of claim 5, wherein the supernatant is from a Chinese Hamster Ovary (CHO) cell culture.

8. The method of claim 1, wherein the contaminant comprises fragments or aggregates of the protein of interest.

9. The method of claim 1, wherein the protein of interest is an antibody.

10. The method of claim 9, wherein the antibody is a monoclonal antibody.

11. The method of claim 10, wherein the monoclonal antibody is selected from the group consisting of a human, humanized and chimeric antibody.

12. The method of claim 1, wherein the second pH is about 0.1, 0.2, 0.3, 0.4, 0.5 or 0.6 pH units less than the pI of the most acidic isoform of the protein of interest.

13. The method of claim 1, wherein the third pH is less than the first pH.

* * * * *